United States Patent
Riehl et al.

(10) Patent No.: US 8,246,529 B2
(45) Date of Patent: Aug. 21, 2012

(54) MAGNETIC CORE FOR MEDICAL PROCEDURES

(75) Inventors: Mark Edward Riehl, Doylestown, PA (US); Kenneth Ghiron, Allentown, PA (US); Leo P. Carbonneau, Nashua, NH (US); Gerard E. Bachand, Cherry Valley, MA (US)

(73) Assignee: Neuronetics, Inc., Malvern, PA (US)

(*) Notice: Subject to any disclaimer, the term of this patent is extended or adjusted under 35 U.S.C. 154(b) by 1 day.

(21) Appl. No.: 12/892,980

(22) Filed: Sep. 29, 2010

(65) Prior Publication Data

US 2011/0015464 A1 Jan. 20, 2011

Related U.S. Application Data

(62) Division of application No. 11/191,106, filed on Jul. 27, 2005, now Pat. No. 7,824,324.

(51) Int. Cl.
*A61N 2/00* (2006.01)

(52) U.S. Cl. .......................................... 600/9
(58) Field of Classification Search ............... 600/9–15
See application file for complete search history.

(56) References Cited

U.S. PATENT DOCUMENTS

| | | |
|---|---|---|
| 3,197,678 A | 7/1965 | Primas |
| 3,658,051 A | 4/1972 | MacLean |
| 3,683,923 A | 8/1972 | Anderson |
| 4,022,701 A | 5/1977 | Sawa et al. |
| 4,156,882 A | 5/1979 | Delagi et al. |
| 4,473,074 A | 9/1984 | Vassiliadis |
| 4,601,753 A | 7/1986 | Soileau et al. |
| 4,638,798 A | 1/1987 | Shelden et al. |
| 4,712,558 A | 12/1987 | Kidd et al. |
| 4,994,015 A | 2/1991 | Cadwell |
| 4,995,395 A | 2/1991 | Ilmoniemi et al. |
| 5,063,011 A | 11/1991 | Rutz et al. |
| 5,078,674 A | 1/1992 | Cadwell |
| 5,097,833 A | 3/1992 | Campos |
| 5,116,304 A | 5/1992 | Cadwell |
| 5,154,723 A | 10/1992 | Kubota et al. |
| 5,160,447 A | 11/1992 | Ishikawa et al. |
| 5,178,757 A | 1/1993 | Corney |
| 5,211,896 A | 5/1993 | Ward et al. |

(Continued)

FOREIGN PATENT DOCUMENTS

EP  0 998 958 A3  5/2000

(Continued)

OTHER PUBLICATIONS

Awiszus et al., "Characterization of Paired-Pulse Transcranial Magnetic Stimulation Conditions Yielding Intracortical Inhibition of I-Wave Facilitation using a Threshold Paradigm", Experimental Brain Research, Nov. 1999, 129(2), 317-324.

(Continued)

*Primary Examiner* — John Lacyk
(74) *Attorney, Agent, or Firm* — Condo Roccia LLP

(57) ABSTRACT

The inventive technique include a system, method and device for treating a patient. The inventive system includes a magnetic field generating device created using a powdered ferromagnetic. The system further includes a circuit in electrical communication with the magnetic core, and a power source in electrical communication with the circuit. The ferromagnetic powder core may be manufactured by at least one of the following: machining, pressing, molding, gluing, and extruding. Also, the ferromagnetic powder core may have a distributed gap structure, where the gap structure operates to focus the magnetic field between pole faces of the magnetic device.

32 Claims, 16 Drawing Sheets

U.S. PATENT DOCUMENTS

| | | | |
|---|---|---|---|
| 5,254,123 A | 10/1993 | Bushey | |
| 5,268,140 A | 12/1993 | Rutz et al. | |
| 5,299,569 A | 4/1994 | Wernicke et al. | |
| 5,370,117 A | 12/1994 | McLaurin, Jr. | |
| 5,543,174 A | 8/1996 | Rutz | |
| 5,566,681 A | 10/1996 | Manwaring et al. | |
| 5,591,373 A | 1/1997 | Ward et al. | |
| 5,655,534 A | 8/1997 | Ilmoniemi | |
| 5,707,334 A | 1/1998 | Young | |
| 5,725,471 A | 3/1998 | Davey et al. | |
| 5,769,778 A | 6/1998 | Abrams et al. | |
| 5,812,301 A | 9/1998 | Nakamura et al. | |
| 5,813,970 A | 9/1998 | Abrams et al. | |
| 5,820,623 A | 10/1998 | Ng | |
| 5,828,770 A | 10/1998 | Leis et al. | |
| 5,855,582 A | 1/1999 | Gildenberg | |
| 5,898,253 A | 4/1999 | El-Antably et al. | |
| 5,923,417 A | 7/1999 | Leis | |
| 6,002,251 A | 12/1999 | Sun | |
| 6,057,373 A | 5/2000 | Fogel | |
| 6,061,644 A | 5/2000 | Leis | |
| 6,066,084 A | 5/2000 | Edrich et al. | |
| 6,074,385 A | 6/2000 | Klopotek | |
| 6,086,525 A | 7/2000 | Davey et al. | |
| 6,117,066 A | 9/2000 | Abrams et al. | |
| 6,132,361 A | 10/2000 | Epstein et al. | |
| 6,155,966 A | 12/2000 | Parker | |
| 6,169,963 B1 | 1/2001 | Markov | |
| 6,179,769 B1 | 1/2001 | Ishikawa et al. | |
| 6,179,771 B1 | 1/2001 | Mueller | |
| 6,198,958 B1 | 3/2001 | Ives et al. | |
| 6,205,356 B1 | 3/2001 | Holcomb | |
| 6,210,317 B1 | 4/2001 | Bonlie et al. | |
| 6,253,109 B1 | 6/2001 | Gielen | |
| 6,256,531 B1 | 7/2001 | Ilmoniemi et al. | |
| 6,266,556 B1 | 7/2001 | Ives et al. | |
| 6,279,579 B1 | 8/2001 | Riaziat et al. | |
| 6,288,785 B1 | 9/2001 | Frantz et al. | |
| 6,355,049 B1 | 3/2002 | Gill | |
| 6,366,814 B1 | 4/2002 | Boveja et al. | |
| 6,389,318 B1 | 5/2002 | Zarinetchi et al. | |
| 6,402,678 B1 | 6/2002 | Fischell et al. | |
| 6,413,263 B1 | 7/2002 | Lobdill et al. | |
| 6,418,345 B1 | 7/2002 | Tepper et al. | |
| 6,425,852 B1 | 7/2002 | Epstein et al. | |
| 6,463,328 B1 | 10/2002 | John | |
| 6,477,410 B1 | 11/2002 | Henley et al. | |
| 6,480,743 B1 | 11/2002 | Kirkpatrick et al. | |
| 6,484,059 B2 | 11/2002 | Gielen | |
| 6,488,617 B1 | 12/2002 | Katz | |
| 6,497,648 B1 | 12/2002 | Rey | |
| 6,500,110 B1 | 12/2002 | Davey et al. | |
| 6,503,187 B1 | 1/2003 | Ilmoniemi et al. | |
| 6,516,213 B1 | 2/2003 | Nevo | |
| 6,516,288 B2 | 2/2003 | Bagne | |
| 6,537,197 B1 | 3/2003 | Ruohonen et al. | |
| 6,551,233 B2 | 4/2003 | Perreault et al. | |
| 6,553,326 B1 | 4/2003 | Kirsch et al. | |
| 6,560,490 B2 | 5/2003 | Grill et al. | |
| 6,567,702 B1 | 5/2003 | Nekhendzy et al. | |
| 6,571,123 B2 | 5/2003 | Ives et al. | |
| 6,572,528 B2 | 6/2003 | Rohan et al. | |
| 6,618,614 B1 | 9/2003 | Chance | |
| 6,625,563 B2 | 9/2003 | Kirsch et al. | |
| 6,629,935 B1 | 10/2003 | Miller et al. | |
| 6,641,520 B2 | 11/2003 | Bailey et al. | |
| 6,663,556 B2 | 12/2003 | Barker | |
| 6,827,681 B2 | 12/2004 | Tanner et al. | |
| 6,849,040 B2 | 2/2005 | Ruohonen et al. | |
| 6,954,060 B1 | 10/2005 | Edel | |
| 6,978,179 B1 | 12/2005 | Flagg et al. | |
| 7,367,935 B2 | 5/2008 | Mechlenburg et al. | |
| 7,367,936 B2 | 5/2008 | Myers et al. | |
| 7,407,478 B2 | 8/2008 | Zangen et al. | |
| 7,560,058 B2 | 7/2009 | Riehl et al. | |
| 2001/0002441 A1 | 5/2001 | Boueja | |
| 2001/0012912 A1 | 8/2001 | Feucht | |
| 2001/0016977 A1 | 8/2001 | Moro et al. | |
| 2001/0018547 A1 | 8/2001 | Mechlenburg et al. | |
| 2001/0031906 A1 | 10/2001 | Ishikawa et al. | |
| 2002/0013612 A1 | 1/2002 | Whitehurst | |
| 2002/0087201 A1 | 7/2002 | Firlik et al. | |
| 2002/0091419 A1 | 7/2002 | Firlik et al. | |
| 2002/0103515 A1 | 8/2002 | Davey et al. | |
| 2002/0123780 A1 | 9/2002 | Grill et al. | |
| 2002/0160436 A1 | 10/2002 | Markov et al. | |
| 2002/0169355 A1 | 11/2002 | Rohan et al. | |
| 2003/0004392 A1 | 1/2003 | Tanner et al. | |
| 2003/0023159 A1 | 1/2003 | Tanner | |
| 2003/0028072 A1 | 2/2003 | Fischell et al. | |
| 2003/0050527 A1 | 3/2003 | Fox et al. | |
| 2003/0065243 A1 | 4/2003 | Tanner | |
| 2003/0073899 A1 | 4/2003 | Ruohonen et al. | |
| 2003/0074032 A1 | 4/2003 | Gliner et al. | |
| 2003/0082507 A1 | 5/2003 | Stypulkowski | |
| 2003/0087264 A1 | 5/2003 | Kaplitt et al. | |
| 2003/0088274 A1 | 5/2003 | Gliner et al. | |
| 2003/0097161 A1 | 5/2003 | Firlik et al. | |
| 2003/0125786 A1 | 7/2003 | Gliner et al. | |
| 2003/0130706 A1 | 7/2003 | Sheffield et al. | |
| 2003/0195588 A1 | 10/2003 | Fischell et al. | |
| 2003/0204135 A1 | 10/2003 | Bystritsky | |
| 2004/0010177 A1 | 1/2004 | Rohan et al. | |
| 2004/0019370 A1 | 1/2004 | Gliner et al. | |
| 2004/0051279 A1 | 3/2004 | Grant et al. | |
| 2004/0077921 A1 | 4/2004 | Becker et al. | |
| 2004/0077923 A1 | 4/2004 | Frimerman et al. | |
| 2004/0122281 A1 | 6/2004 | Fischell et al. | |
| 2004/0127942 A1 | 7/2004 | Yomtov et al. | |
| 2004/0138524 A1 | 7/2004 | Ueda et al. | |
| 2004/0138550 A1 | 7/2004 | Hartlep et al. | |
| 2004/0143300 A1 | 7/2004 | Rogers | |
| 2004/0153129 A1 | 8/2004 | Pless et al. | |
| 2004/0167592 A1 | 8/2004 | Grove | |
| 2004/0172012 A1 | 9/2004 | Otsuka et al. | |
| 2004/0193001 A1 | 9/2004 | Miller | |
| 2004/0193002 A1 | 9/2004 | Tanner | |
| 2004/0204625 A1 | 10/2004 | Riehl et al. | |
| 2005/0021104 A1 | 1/2005 | DiLorenzo | |
| 2005/0124848 A1 | 6/2005 | Holzner | |
| 2005/0212162 A1 | 9/2005 | Aisenbrey | |
| 2005/0216071 A1 | 9/2005 | Devlin et al. | |
| 2005/0228209 A1 | 10/2005 | Schneider et al. | |
| 2005/0234286 A1 | 10/2005 | Riehl et al. | |
| 2005/0256539 A1 | 11/2005 | George et al. | |
| 2006/0052687 A1 | 3/2006 | Ruohonen | |
| 2006/0113696 A1 | 6/2006 | Aisenbrey | |
| 2006/0199992 A1 | 9/2006 | Eisenberg et al. | |
| 2009/0240096 A1 | 9/2009 | Riehl et al. | |

FOREIGN PATENT DOCUMENTS

| | | |
|---|---|---|
| EP | 1145738 A2 | 10/2001 |
| EP | 1 273 320 A1 | 1/2003 |
| JP | 2000-504966 | 4/2000 |
| JP | 2001-526947 A | 12/2001 |
| JP | 2003-180649 | 7/2003 |
| WO | WO 98/06342 | 2/1998 |
| WO | WO 99/33516 A1 | 7/1999 |
| WO | WO 99/64884 | 12/1999 |
| WO | WO 00/74777 A1 | 12/2000 |
| WO | WO 01/12236 A2 | 2/2001 |
| WO | WO 01/28622 A2 | 4/2001 |
| WO | WO 01/97906 A2 | 12/2001 |
| WO | WO 02/09811 A1 | 2/2002 |
| WO | WO 02/31604 A1 | 4/2002 |
| WO | WO 02/32504 A2 | 4/2002 |
| WO | WO 02/072194 A2 | 9/2002 |
| WO | WO 02/085449 A2 | 10/2002 |
| WO | WO 02/085454 A1 | 10/2002 |
| WO | WO 02/089902 A2 | 11/2002 |
| WO | WO 02/094997 A2 | 11/2002 |
| WO | WO 03/035163 A2 | 5/2003 |
| WO | WO 03/039468 A2 | 5/2003 |
| WO | WO 03/082405 A1 | 10/2003 |
| WO | WO 03/084605 | 10/2003 |
| WO | WO 03/085546 A1 | 10/2003 |
| WO | WO 03/090604 A2 | 11/2003 |

| | | |
|---|---|---|
| WO | WO 03/098268 A1 | 11/2003 |
| WO | WO 2004/006750 A2 | 1/2004 |
| WO | WO 2004/082759 A2 | 9/2004 |
| WO | WO 2004/100765 A2 | 11/2004 |
| WO | WO 2005/000401 A1 | 1/2005 |
| WO | WO 2005/065768 A1 | 7/2005 |
| WO | WO 2005/067610 A2 | 7/2005 |

OTHER PUBLICATIONS

Baudewig et al., "Functional MRI of Cortical Activations Induced by Transcranial Magnetic Stimulation (TMS)", Brain Imaging-Neuro Report, Nov. 16, 2001, 12(16), 3543-3548.

Bohning et al., "A Combined TMS/fMRI Study of Intensity-Dependant TMS over Motor Cortex", Society of Biological Psychiatry, Feb. 15, 1999, 45(4), 385-394.

Bohning et al., "A TMS Coil Positioning/Holding System for MR Image-Guided TMS Interleaved with fMRI", Clinical Neurophysiology, Nov. 2003, 114(11), 2210-2219.

Bohning et al., "BOLD-fMRI Response to Single-Pulse Transcranial Magnetic Stimulation (TMS)", Journal of Magnetic Resonance Imaging, Jun. 2000, 11(6), 569-574.

Garcia-Toro et al., "Modest Adjunctive Benefit with Transcranial Magnetic Stimulation in Medication-Resistant Depression", Journal of Affective Disorders, May 2001, 64(2-3), 271-275.

George and Belmaker (Eds.) Grafman, "TMS as a Primary Brain Mapping Tool", Transcranial Magnetic Stimulation in Neuropsychiatry, First Edition, American Psychiatric Press, 2000, pp. 115-140.

George and Belmaker (Eds.), Lorberbaum et al., "Safety Concerns of TMS", Transcranial Magnetic Stimulation in Neuropsychiatry, First Edition, American Psychiatric Press, 2000, 141-161.

George et al., "A Controlled Trial of Daily Left Prefrontal Cortex TMS for Treating Depression", Society of Biological Psychiatry, Nov. 15, 2000, 48(10), 962-970.

George, "New Methods of Minimally Invasive Brain Modulation as Therapies in Psychiatry: TMS, MST, VNS and DBS", Chinese Medical Journal (Taipei), Aug. 2002, 65(8), 349-360.

Greene, APA Meeting, "Electromagnetic Stimulation Relieves Depression", http://HealthyPlace.com, May 17, 1999, 3 pages.

Hess et al., "Magnetic Stimulation of the Human Brain: Influence of Size and Shape of the Stimulating Coil", Motor Disturbances II, May 1990, 3, 31-42.

Keiji et al., "Effects of Transcranial Magnetic Stimulation on EEG Activity", IEEE transactions on Magnetics, Sep. 2002, 38(5), 3347-3349.

Lisanby et al., "Magnetic Seizure Therapy of Major Depression", Arch Gen Psychiatry, Mar. 2001, 58, 303-307.

Lisanby et al., "Sham TMS: Intracerebral Measurement of the Induced Electrical Field and the Induction of Motor-Evoked Potentials", Society of Biological Psychiatry, Mar. 1, 2001, 49(5), 460-463.

Lisanby, "Safety and Feasibility of Magnetic Seizure Therapy (MST) in Major Depression: Randomized Within-Subject Comparison with Electroconvulsive Therapy", Neuropsychopharmacology, New York State Psychiatric Institute, Jul. 2003, 28(10), 1852-1865.

Lisanby, "Update on Magnetic Seizure Therapy: A Novel Form of Convulsive Therapy", The Journal of ECT, Dec. 2002, 18(4), 182-188.

Loo et al., "Transcranial Magnetic Stimulation (TMS) in Controlled Treatment Studies: Are Some "Sham" Forms Active?", Society of Biological Psychiatry, Feb. 15, 2000, 47(4), 325-331.

Nahas et al., "Left Prefrontal Transcranial Magnetic Stimulation (TMS) Treatment of Depression in Bipolar Affective Disorder: A Pilot Study of Acute Safety and Efficacy", Bipolar Disorders, Feb. 2003, 5(1), 40-47.

Nahas et al., "Safety and Feasibility of Repetitive Transcranial Magnetic Stimulation in the Treatment of Anxious Depression in Pregnancy: A Case Report", J. Clin Psychiatry, Jan. 1999, 60, 50-52.

Nahas et al., "Unilateral Left Prefrontal Transcranial Magnetic Stimulation (TMS) Produces Intensity-Dependent Bilateral Effects as Measured by Interleaved BOLD fMRI", Society of Biological Psychiatry, Nov. 1, 2001, 50(9), 712-720.

Pascual-Leone et al., "Rapid-Rate Transcranial Magnetic Stimulation of Left Dorsolateral Prefrontal Cortex in Drug-Resistant Depression", The Lancet, Jul. 27, 1996, 348(9022), 233-237.

Pridmore, "Rapid Transcranial Magnetic Stimulation and Normalization of the Dexamethasone Suppression Test", Psychiatry and Clinical Neurosciences, Feb. 1999, 53(1), 33-37.

Roth et al., "A Coil Design for Transcranial Magnetic Stimulation of Deep Brain Regions", Journal of Clinical Neurophysiology, Aug. 2002, 19(4), 361-370.

Ruohonen, "Electroencephalography Combined with TMS", BioMag Laboratory, Helsinki University Central Hospital, http://www.biomag.helsinki.fi/tms/TMSEEG.html, Oct. 6, 1999, 22 pages.

Sommer et al., "Increased Transcranial Magnetic Motor Threshold after ECT", European Archives of Psychiatry and Clinical Neuroscience, Oct. 2002, 252(5), 250-252.

Terrace et al., "The Cognitive Effects of Electroconvulsive Shock and Magnetic Seizure Therapy in Rhesus Monkeys", Society for Neuroscience Abstract Viewer and Itinerary Planner, Dec. 2002, Abstract Only # 536.7.

Trivedi, "Treatment-Resistant Depression: New Therapies on the Horizon", Annals of Clinical Psychiatry, Mar. 2003, 15(1), 59-70.

Wassermann, "Repetitive Transcranial Magnetic Stimulation: An Introduction and Overview", CNS Spectrums, The International Journal of Neuropsychiatric Medicine, Jan. 1997, 7 pages.

MAGNETIC CORE FOR MEDICAL PROCEDURES

CROSS REFERENCE TO RELATED APPLICATIONS

This application is a division of application Ser. No. 11/191,106, filed Jul. 27,2005 now U.S. Pat. No. 7,824,324, entitled "MAGNETIC CORE FOR MEDICAL PROCEDURES," the contents of which is incorporated herein in its entirety.

BACKGROUND

A number of medical ailments are treated or treatable and/or diagnosed through the application of a magnetic field to an afflicted portion of a patient's body. Neurons and muscle cells are a form of biological circuitry that carry electrical signals and respond to electromagnetic stimuli. When an ordinary conductive wire loop is passed through a magnetic field or is in the presence of a changing magnetic field, an electric current is induced in the wire.

The same principle holds true for conductive biological tissue. When a changing magnetic field is applied to a portion of the body, neurons may be depolarized and stimulated. Muscles associated with the stimulated neurons can contract as though the neurons were firing by normal causes.

A nerve cell or neuron can be stimulated in a number of ways, including transcutaneously via transcranial magnetic stimulation (TMS), for example. TMS uses a rapidly changing magnetic field to induce a current on a nerve cell, without having to cut or penetrate the skin. The nerve is said to "fire" when a membrane potential within the nerve rises with respect to its normal negative ambient level of approximately −90 millivolts, depending on the type of nerve and local pH of the surrounding tissue.

The use of magnetic stimulation is very effective in rehabilitating injured or paralyzed muscle groups. Apart from stimulation of large muscle groups such as the thigh or the abdomen, experimentation has been performed in cardiac stimulation as well. In this context, magnetic stimulation of the heart may prove to be superior to CPR or electrical stimulation, because both of those methods undesirably apply gross stimulation to the entire heart all at once.

Another area in which magnetic stimulation is proving effective is treatment of the spine. The spinal cord is difficult to access directly because vertebrae surround it. Magnetic stimulation may be used to block the transmission of pain via nerves in the back, e.g., those responsible for lower back pain.

Magnetic stimulation also has proven effective in stimulating regions of the brain, which is composed predominantly of neurological tissue. One area of particular interest is the treatment of depression. It is believed that more than 28 million people in the United States alone suffer from some type of neuropsychiatric disorder. These include conditions such as depression, schizophrenia, mania, obsessive-compulsive disorder, panic disorders, and others. Depression is the "common cold" of psychiatric disorders, believed to affect 19 million people in the United States and possibly 340 million people worldwide.

Modern medicine offers depression patients a number of treatment options, including several classes of anti-depressant medications (e.g., SSRI's, MAOI's and tricyclics), lithium, and electroconvulsive therapy (ECT). Yet many patients remain without satisfactory relief from the symptoms of depression. To date, ECT remains an effective therapy for resistant depression; however, many patients will not undergo the procedure because of its severe side effects.

Recently, repetitive transcranial magnetic stimulation (rTMS) has been shown to have significant anti-depressant effects for patients that do not respond to the traditional methods. The principle behind rTMS is to apply a subconvulsive stimulation to the prefrontal cortex in a repetitive manner, causing a depolarization of cortical neuron membranes. The membranes are depolarized by the induction of small electric fields in excess of 1 V/cm that are the result of a rapidly changing magnetic field applied non-invasively.

Creation of the magnetic field has been varied. Certain techniques describe the use of a coil to create the necessary magnetic field. Other techniques contemplate the use of a high saturation level magnetic core material, like vanadium permendur. Use of the magnetic core material, as compared to the coil or so-called "air" core solution, has been shown to increase the efficiency of the TMS process. For example, as discussed with reference to U.S. Pat. No. 5,725,471, using a magnetic core instead of just a coil increases the efficiency of the TMS process by creating a larger, more focused magnetic field with the same or lesser input power requirements.

This advance has allowed a more cost effective solution that uses existing 120 volt power without complicated and a costly power supplies. Also, because of the need for the same or lesser power inputs, the magnetic core significantly reduces the undesirable heating that was associated with the coil solution and created a safety risk for patients. For example, magnetic core devices in comparison to coil-only devices reduce the magnetic reluctance path by a factor of two. This reluctance reduction translates into a reduction of required current to generate the same magnetic field by the same factor, and thus provides a fourfold reduction in required power.

The ferromagnetic core alternatives typically are fabricated by laminating layers of silicon steel or similar ferromagnetic metal together to form the core structure. The layers may be constructed by stacking cut-out shapes or by winding a ribbon of material onto a mandrel followed by further machining and processing to attain the desired core geometry.

While solutions fabricated using these ferromagnetic cores offered a marked improvement over their coil-only counterparts, the ferromagnetic cores also suffer from certain complexities in their construction and limitations in their geometry. Specifically, the stacked layer construction method does not provide optimal alignment of the metal crystal structure with the magnetic flux lines and also requires a controlled lamination process to guarantee minimal eddy current losses. The wound ribbon construction method typically results in a core with arc-shaped or C-shaped structure having a certain radius and span. The dimensions and geometry of these ferromagnetic cores are selected to ensure desired depth of penetration, magnetic field shape and appropriate magnetic field magnitude at certain locations within the patient's anatomy.

The ferromagnetic core's construction method involves a complex and meticulous construction process that increased both the complexity and cost of the core. For example, because ferromagnetic material is electrically conductive, eddy currents are established in the material when it is exposed to a rapidly varying magnetic field. These eddy currents not only heat the core material through resistive heating, but they also produce an opposing magnetic field that diminishes the primary magnetic field. To prevent these losses the eddy current pathways are broken by fabricating the core from very thin layers or sheets of ferromagnetic material that are electrically isolated from each other.

The sheets typically are individually varnished or otherwise coated to provide insulation between the sheets, thus preventing current from circulating between sheets and resulting in reduced eddy current losses. Also, the sheets are oriented parallel to the magnetic field to assure low reluctance.

The wound core fabrication process begins by winding a long thin ribbon of saturable ferromagnetic material, such as vanadium permendur or silicon steel, on a mandrel to create the desired radius, thickness and depth of the core. Each side of the ribbon typically is coated with a thin insulative coating to electrically isolate it. Once the ribbon has been wound on the mandrel to the desired dimensions, it is removed from the mandrel and dipped in epoxy to fix its position. Once the epoxy has cured, a sector of the toroidal core is cut with a band saw and removed, thus forming the desired arc-shape. Because the cutting process may reduce the electrical isolation of adjacent laminations, each cut is finely ground so that it is smooth, and then a deep acid etch is performed. The deep etch is performed by dipping each of the cut ends in an acid bath. This removes any ferromagnetic material that may be shorting the laminations. Following the deep etch, the faces are coated to prevent oxidation and to maintain the shape and structural integrity of the core. The manufacturing process of cutting, coating, aligning, attaching and laminating the layers makes for a complex and costly manufacturing process. Also, these considerations make it difficult to change or customize the shape of the core structure.

Winding a coil of insulated wire around the ferromagnetic core to deliver the current needed to create the magnetic field also is a complex and detailed process. A typical inductance for a core of this type is about 15-20 microHenries. Each pass of the winding around the core must be made at precise intervals on the core structure. In the simplest configuration, each core has only one winding, although typically the core may be wound multiple times.

While the present ferromagnetic core shape and composition work well, and certainly better than the coil-only approach, it should be appreciated that other core compositions and core shapes may work equally well under other circumstances.

SUMMARY

The inventive technique include a system, method and device for treating a patient. The inventive system includes a magnetic field generating device created using a powdered ferromagnetic. The system further includes a circuit in electrical communication with the magnetic core, and a power source in electrical communication with the circuit. The ferromagnetic powder core may be manufactured by at least one of the following: machining, pressing, molding, gluing, and extruding. Also, the ferromagnetic powder core may have a distributed gap structure, where the gap structure operates to focus the magnetic field between pole faces of the magnetic device. The ferromagnetic powder core may have a shaded pole face, where the pole face comprises a channel cut into the face of the pole with a shorted turn inserted into the channel. The ferromagnetic powder core may comprise a ferromagnetic electrically conductive material such as iron or a non-ferromagnetic material such as copper, brass and/or aluminum, for example. Also, the system may include a wire or conductor that is wound around a bobbin structure that acts to insulate the wire from the core structure.

The inventive method of treating a patient includes creating a magnetic field using a magnetic device having a non-linear ferromagnetic powder core and applying the magnetic field to the patient to treat the patient as a function of the magnetic field. The inventive method further may use a ferromagnetic powder core that has a distributed gap structure that focuses the magnetic field between pole faces of the magnetic device via the distributed gap core structure. The ferromagnetic powder core may include a ferromagnetic electrically conductive material such as iron and/or a non-ferromagnetic material such as copper, brass and aluminum.

DETAILED DESCRIPTION

Figure 1A:
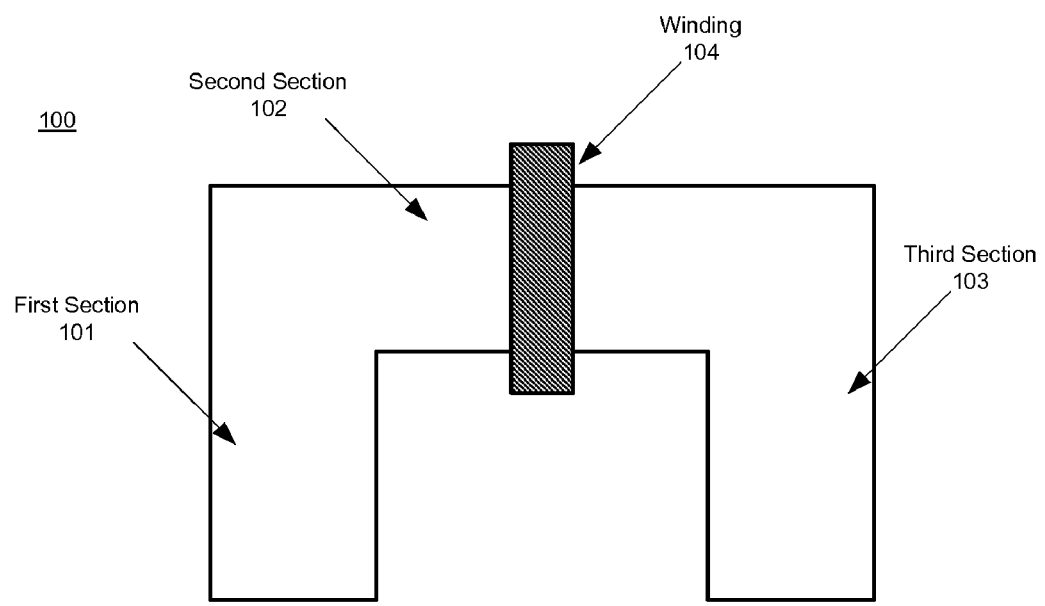
FIGS. 1 through 13 illustrate example core shapes and configurations, in accordance with the invention.

In one embodiment of the invention, a distributed gap core structure is contemplated, for example an air gap core structure. It should be appreciated that the air gap core refers to the internal structure of a magnetic core, while the "air core" discussed in the Background of the Invention section refers to a winding without any magnetic core. One type of distributed air gap core structure is created by dispersing powdered ferromagnetic particles in a matrix of insulating material. It should be appreciated that the invention is not limited to an ferromagnetic powder core, but various embodiments may include any gap core structure. The gap core structure may be any structure where one or more conductive particles are insulated (or nearly so) from each other.

The use of distributed gap core structures, like powdered ferromagnetic core materials reduces the complex manufacturing and corresponding cost burden inherent in the laminated structures. In addition, because of the insulating material that separates the ferromagnetic particles in the core material, the core is less conductive, and as a result eddy current losses are minimal. More specifically, the non-conductive gaps may prohibit the flow of current from one ferromagnetic particle to the next, and thus reduce overall current flow in the core. Because eddy currents result from the conductive flow of current in magnetic materials like the core, reducing the conductive flow serves to reduce the eddy currents. As a result of the reduced eddy currents, the distributed gap core structure produces even less heat than its counterpart ferromagnetic core structures.

Therefore, higher power and current levels may be used to drive coils fabricated with a distributed gap core without concern for heating that may be excessive for a patient undergoing treatment. Moreover, these higher power levels may be achieved without the need for sophisticated cooling systems, typical of the "air" core solutions. In addition, these higher current drive levels may drive the distributed gap cores closer to their saturation level to obtain greater magnetic field strength, without concern for consequent undesirable heating. In fact, in some embodiments, heating due to resistive losses in the windings may be greater than heat generated within the distributed gap core material. In other words, the heating characteristics of the windings may provide the only real heating concerns for patient use.

Reducing eddy current losses and the concomitant reduction in heat generation permits operation of the magnetic core at proportionally higher duty cycles. From a medical application perspective, relatively greater and more intense therapy may be achieved, which may be beneficial for certain applications. In addition to its inherent reduced temperature, the core may additionally be enclosed in a structure that further enhances its thermal performance. For example, by potting the core into a shell heat may be directed to a desirable surface for radiation to the surrounding air. Such a surface may, for example, be located away from surfaces that touch a patient or the operator.

Air spaces and thermal insulation also may be added between the windings or other heat generating materials to insulate them from surfaces that may come in contact with a patient, for example. Typically these surfaces must be kept at or below 41.5 degrees Celsius in order to comply with medical device standards, well known to those skilled in the art.

It also should be appreciated that the reduced current flow and eddy current loss gained with the distributed gap core structure is not found in the cores created by a sintering process. This is due, in part, because the sintering process operates to place the insulated iron powder particles back into electrical conductivity with one another, and thus promote current flow and increased eddy current losses.

The insulative material may be any material that offers a different level of permeability and inductance as compared to the ferromagnetic particles. By introducing an insulative gap, the magnetic flux path is increased, thus reducing the permeability and the inductance of the core material. It may be desirable to have a core with a permeability of greater than 1. Moreover, because the distributed gap reduces eddy currents, there are fewer flux distortions. This relatively greater isotropic structure provides for a more uniformly distributed flux and facilitates more complex and sophisticated core structures.

The ferromagnetic powder used to make the core may be made of particles that are less than 0.05 inch in diameter. Although it should be appreciated that the particles may be of any size in the contemplated embodiments, it should be appreciated that the specific particle dimension is related to the frequency at which the core is to operate. For example, if the core is to be pulsed at a higher frequency, it may be desirable to use particles with a smaller dimension. The ferromagnetic particles may vary in size and may not be spherical but rather irregular in shape. In any event, it should be appreciated that specific particle size may be selected to reduce losses resulting from eddy currents and hysteresis losses within individual particles.

Also, although the invention is not limited to any particular formation, it should be appreciated that individual ferromagnetic particles may be formulated from iron, iron alloys and amalgams of other conductive or partially conductive materials. Also, the material composition of the particles may include non-ferrous metals such as copper, brass, aluminum and alloying elements such as carbon, silicon, nickel and chromium formulated to create the desired crystal structure and desired magnetic characteristics. Saturation, permeability and B-H curve characteristics vary depend on this selected formulation. In addition, the ferromagnetic particles may be coated with a non-conductive resin to, among other things, prevent oxidation while being stored before the coated particles are formed into the desired structure in the core manufacturing process.

The contemplated embodiments include a method for manufacturing a magnetic core device, for example a powdered ferromagnetic core device. The method includes selecting certain powdered ferromagnetic materials. The materials are then mixed and compressed to form the core. The powder may be pressed into a mold having the final form of the core. Alternatively, blocks of compressed material can be manufactured and subsequently machined to the desired geometry. Also, separate molded or machined component pieces may be mechanically assembled into the final core geometry using cement, heating or bonding by other mechanical means. The ferromagnetic powder core may be produced by any of several processes. For example, stream of molten iron may be atomized by a high pressure water jet.

The ferromagnetic particles may be coated with any appropriate substance. For example, the ferromagnetic particles may be coated with an insulative substance, like alkali metal silicate, for example. The insulative substance provides insulation between each of the particles in the core, and thus creates the distributed gap core. In one embodiment, an aqueous alkali metal silicate solution is used containing up to 39% by weight solids of $K_2O$ and $SiO_2$, and up to 54% by weight solids of $Na_2O$ and $SiO_2$. A wetting agent or surfactant, like alkyl phenoxyl polyethoxy ethanol for example, may be added to facilitate uniform coating of the particles.

The appropriate substances are mixed and may be surface-dried at the same time. A thin coating of an adherent resin may be applied to the ferromagnetic particles. Such resins may include polyimides, fluorocarbons and acrylics. The resin permits the particles to remain flexible and thus capable of withstanding high temperatures without decomposing into conducting residues.

To form the core, the powder is compressed. The compression may be approximately in the range of 25 to 100 tons per square inch. A form may be used to create the desired shape. The pressed components may be annealed, for example, at 500 to 600 degrees Celsius to relieve the stresses and reduce the hysteresis losses.

If ferromagnetic powder is to be used for the magnetic core in such an application, the particles may be insulated from one another, for example, with between 1% to 3% spacing between particles. Although this is just one example. When raw ferromagnetic powder is compressed up to 100 tons per square inch and not sintered, the density remains 1% or 2% below the true density of solid iron, because of residual crevices or interstices which remain empty or are filled with lower density resin. As a result, the ferromagnetic powder may be compressed to about 90% of theoretical density or better in order to have a distributed insulation-containing air gap less than 3% in each of the three orthogonal directions, one of which is that of the flux path. In any of the embodiments, the magnetic core may be a composition that allows the core to saturate at 0.5 Tesla or greater, for example.

During the manufacturing process, the individual ferromagnetic particles in the powder may be mixed with a binding material, for example phenolic or epoxy. The ferromagnetic powder may then be pressed into its final shape. Next, a baking or heating process may be implemented to cure the core material. After the core has been cured, the ferromagnetic particles may be separated by air or insulative binding material which effectively results in a distributed gap. As a result, the gap is distributed throughout the core.

The novel device and techniques may be used for many purposes including the treatment of patients with medical conditions. This applicability will be discussed in the context of TMS in order to provide greater understanding. However, it should be appreciated that techniques have applicability beyond TMS also are contemplated by the invention.

In just one embodiment, a method of treating a patient by creating a magnetic field using a magnetic device having a non-linear core is contemplated. As will be discussed with reference to FIGS. 1-13, the core may assume a number of different and various shapes and sizes. The shapes and sizes may vary with the particular area of the patient's anatomy that needs treatment, as well as the external area of the patient on which the magnet may be placed. For example, in just one embodiment, the core may have a U-shaped structure that facilitates placing the core in close proximity to a patient's head for the purpose of treating the brain with pulsed magnetic fields for the treatment of depression. This may be accomplished, for example, by stimulating tissue (e.g., brain tissue), nerves and/or muscle, for example, from an area relatively proximate to the cutaneous surface and the area of treatment.

Also, the core used to treat the patient may be a gap distributed core and more specifically an ferromagnetic powder core. As discussed, the embodiments are not limited to any compositions, but contemplate any material composition that effectively creates a distributed gap core structure. Also, the embodiments contemplate any type of core structures, including ferromagnetic, where the shape of the core structure has a non-arc shaped structure. For example, the embodiments contemplate the use of a non-sintered core material. Also, other embodiments contemplate a non-linear shaped ferromagnetic powder core.

The magnetic field passing through the core may be applied to the patient for the purpose of treating or diagnosing the patient. The embodiments are not limited to a specific level or intensity of the magnetic field, but instead contemplate any field strength, focus and duration necessary to treat or diagnose the desired patient.

A novel system may include a magnetic field generating device created using a powdered ferromagnetic core, a circuit in electrical communication with the magnetic core, and being drive by a power source in electrical communication with the circuit.

A power source may be provided in order for the core to generate the requisite magnetic field. The power source may be in electrical communication with the windings wrapped around a portion of the core. The power source may be created to provide a substantially constant power or substantially constant current source. For example, the power source may provide a substantially constant power or substantially constant current source to a capacitor, which then discharges to the core to create the magnetic field.

The power source may operate on an alternating current input voltage in the range of 85 volts to 264 volts. In this way, the inventive device may operate using power typically available in residential and commercial settings.

Finally, the embodiments contemplate a method for treating depression. As part of the method a patient is selected who suffering from a depressive disorder. The patient's brain is then magnetically stimulated using a transcranial magnetic stimulator with a magnetic core. The core may be a ferromagnetic core having a U-shaped structure and/or a distributed gap core structure having any core shape and structure.

It should be appreciated that the use of ferromagnetic powder core makes more feasible many possible core geometries. In fact, the distributed gap core (e.g., ferromagnetic powder core) manufacturing process, allows the core's geometry to have an array of possibilities. The precise shape and size of the core's geometry may be made to vary depending upon various factors. For example, although not an exclusive list of considerations, the following may be considered in deciding upon the size and geometry of the core: the use of the core, the available mounting area and volume, the allowable radiation, the limitations on windings, the operating temperature, and how the core will be mounted. Consequently, a core's geometrical shape can take any form, including a cylinder, bobbin, toroid, a non-toroid or several other possible shapes.

In addition, it also should be appreciated that the ferromagnetic powder manufacturing process facilitates construction of the core as multiple components or pieces. Multi-piece ferromagnetic powder cores, each piece made of similar or different magnetic material, may be used for extremely complex shapes or larger core constructions. These individual pieces, of different or similar permeabilities, may be brought together by gluing and/or any other attachment techniques well known to those skilled in the art. This is facilitated, in part, due to the ease of manufacturing and core shaping provided by the powder core process.

In addition, the powder core manufacturing process also facilitates the use of other materials to shape the magnetic field provided by the core structure. For example, it may be desirable to deflect or redirect a certain portion of the created magnetic field away from certain parts of the anatomy. For example, for brain stimulation, it may be desirable to protect the trigeminal nerve from being stimulated and causing discomfort to the patient. This may be accomplished using any number of techniques.

One example technique locates a conductor on a treatment area relative to the protected area. The conductor may act to reduce stimulation of a cutaneous-proximate area on the patient. This may be accomplished by modifying an electric or magnetic field created by the transcutaneous stimulation. Also, it may be accomplished via modification of the electric field through modification of the magnetic flux created by the transcutaneous stimulation.

FIGS. 1 through 13 provide various examples of core shapes and configurations that are facilitated by the contemplated embodiments. It should be appreciated, however, that FIGS. 1 through 13 are not provided in order to detail every possible shape and configuration contemplated by the invention. Instead, the figures merely provide certain examples to aid in an understanding of just a few of the contemplated embodiments.

Generally, it may be noted that the magnetic cores shown in FIGS. 1 through 13 essentially comprise three sections. Although the cores may not have to be separately constructed in three of such sections, describing their shape as such facilitates further discussion of the shape, and thus is not meant to be limiting in any way.

FIG. 1 will be used to discuss the features of the core. As shown in FIG. 1, a core 100 includes a first section 101, a second section 102 and a third section 103. In the context of FIG. 1 which is a squared off U-shape, second section 102 serves as a bridge connecting first section 101 and third section 103, which serve as the posts or poles for the U-shape. First section 101 is joined with second section 102 at a right angle. Similarly, third section 103 is joined with second section 102 at a right angle. It should be appreciated that these sections may be fabricated as one complete pressed part, or they could be individually pressed and later assembled to form the U-shape.

As shown in FIGS. 2 through 13, various other shapes and configurations that may be modifications or minor alterations are depicted in FIG. 1. For example, as shown in FIG. 2, either ends of the first, second and/or third sections may be angled or chamfered. Such angles or chamfering may be accomplished using any such value, for example using an angle of 45 degrees. Such modifications to the shape of the pole face are used by those skilled in the art to redirect and optimize the spatial distribution of the magnetic field for the intended application. Also, the angled sections may be arc-shaped as shown in FIG. 3.

Figure 4:
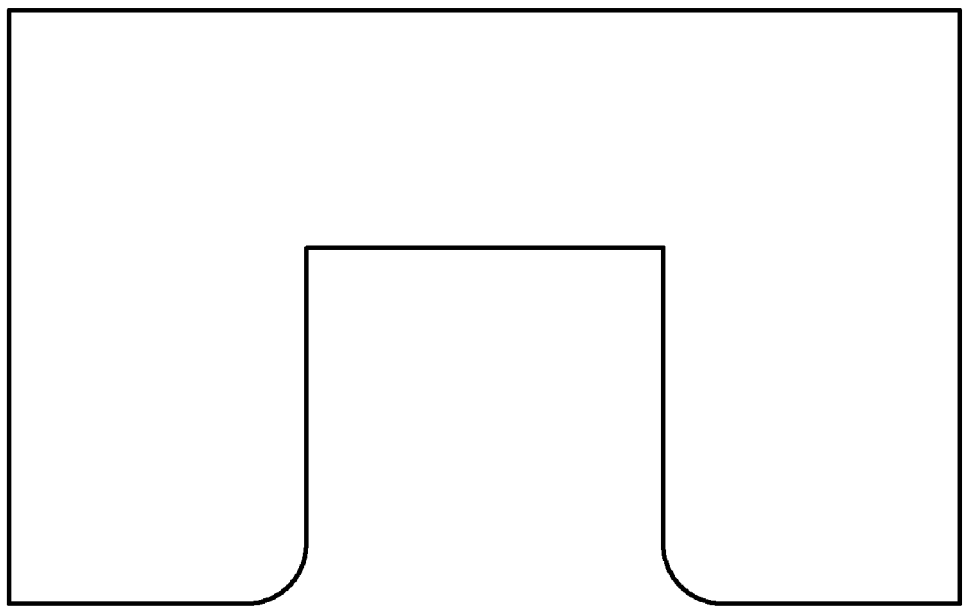
Figure 5:
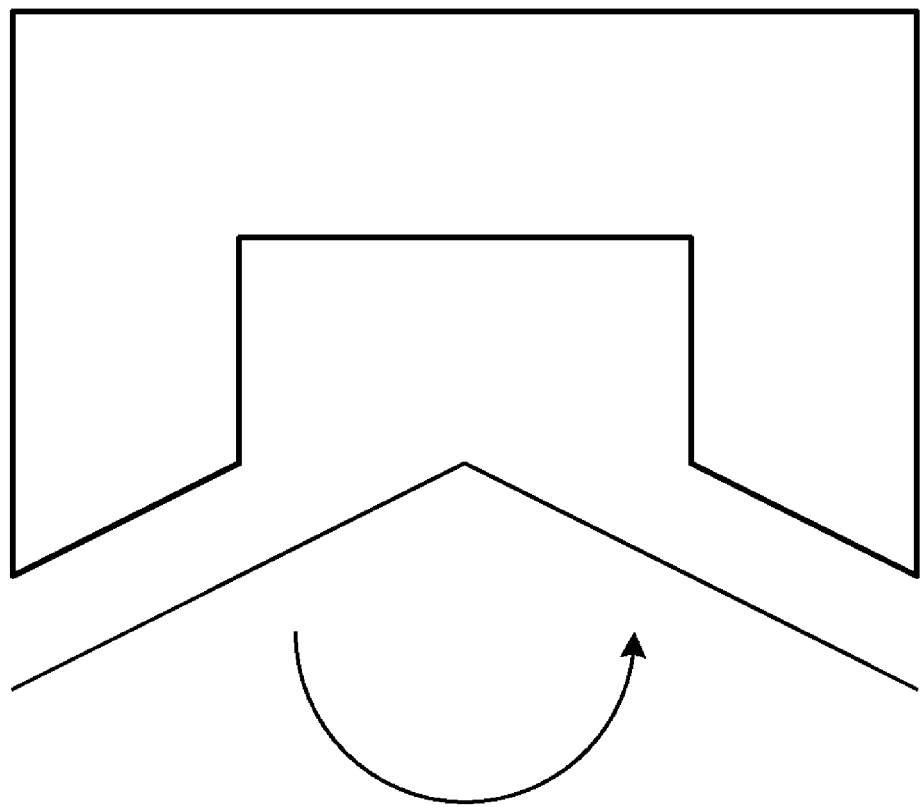
Figure 6:
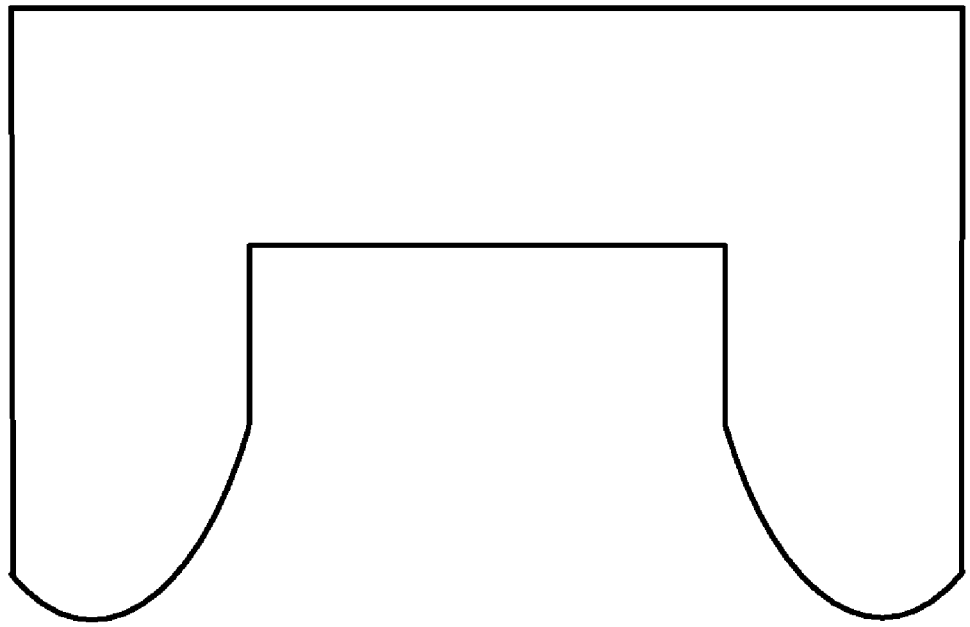
Figure 7:
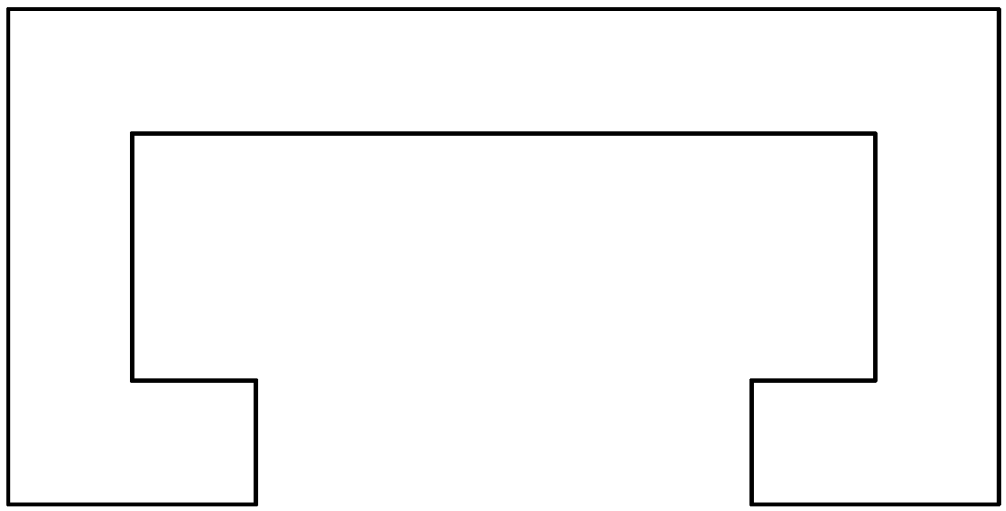
Figure 8:
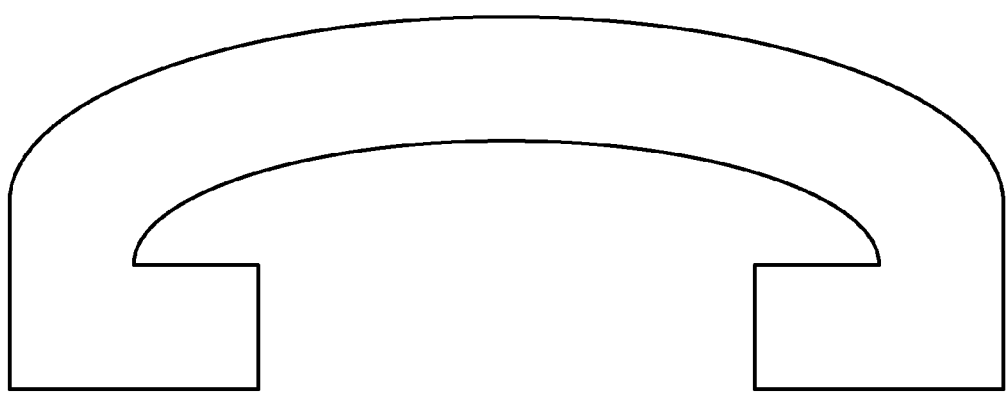
Figure 13:
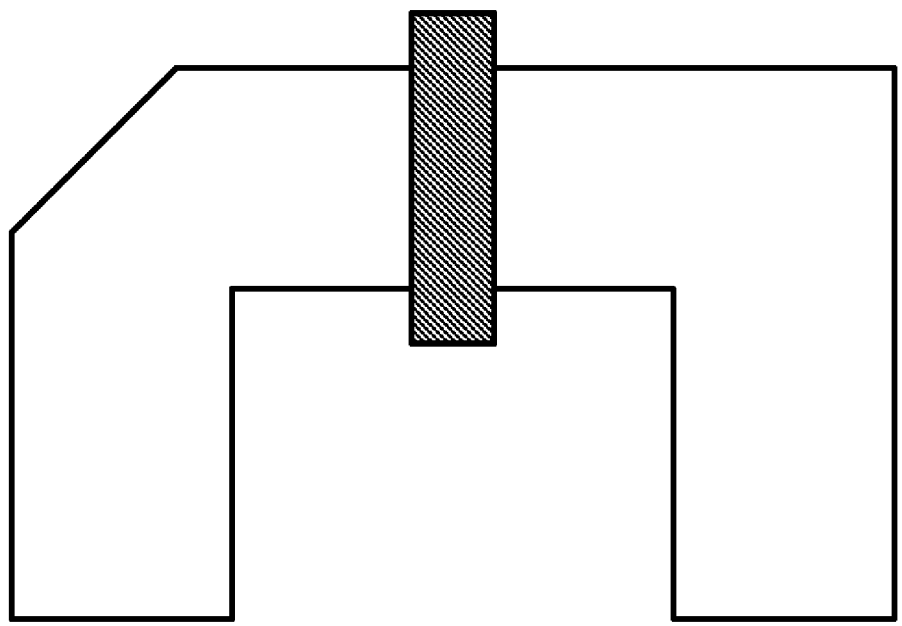

The angles may be made to both the cornered ends of the core as shown in FIG. 2, or on just one of the cornered ends of the core as shown in FIG. 13. Similarly, the angles may be made at the opposite ends with respect to the cornered ends, as shown in FIG. 5. Alternatively, the angles depicted in FIG. 5 may be arc-shaped or smoothed, as shown in FIGS. 4 and 6. Also, the first and third sections may be L-shaped as shown in FIG. 7 with a linear second section, or as shown in FIG. 8 with an arc-shaped second section.

Figure 9:
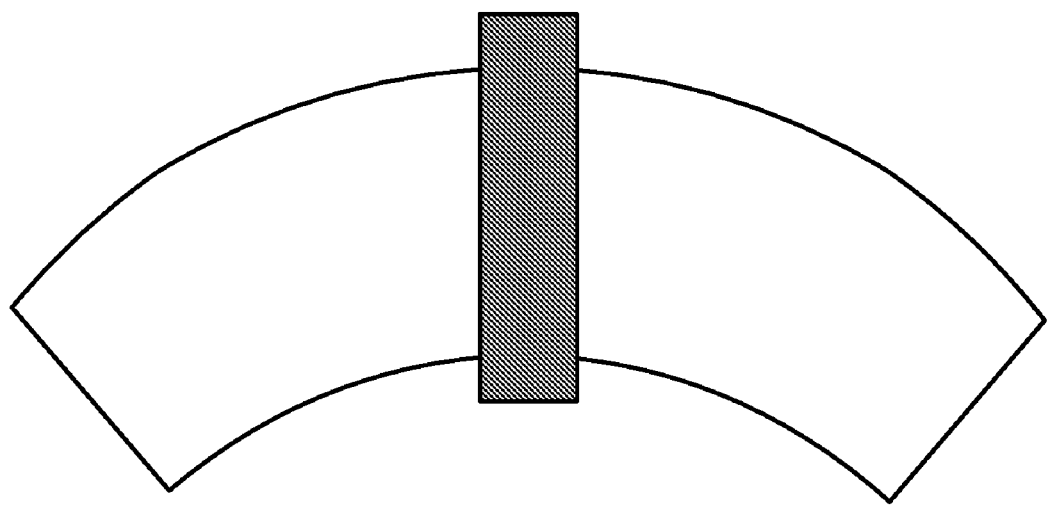
Figure 10:
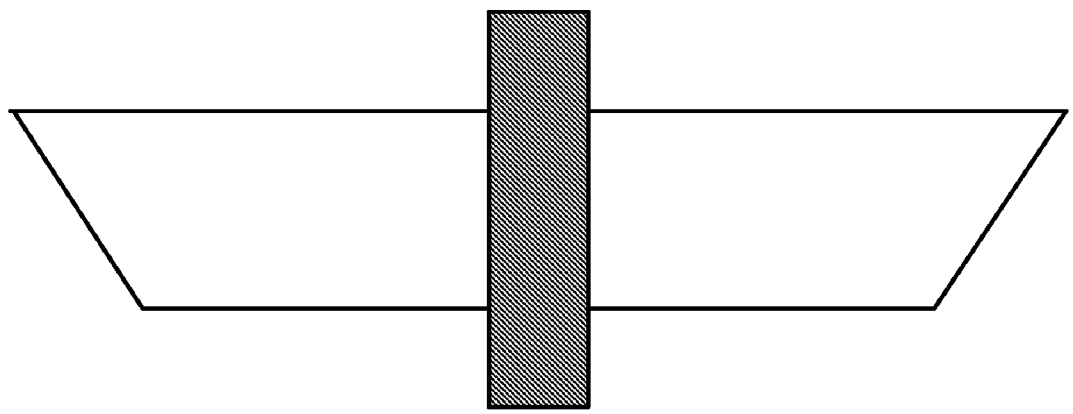
Figure 11:
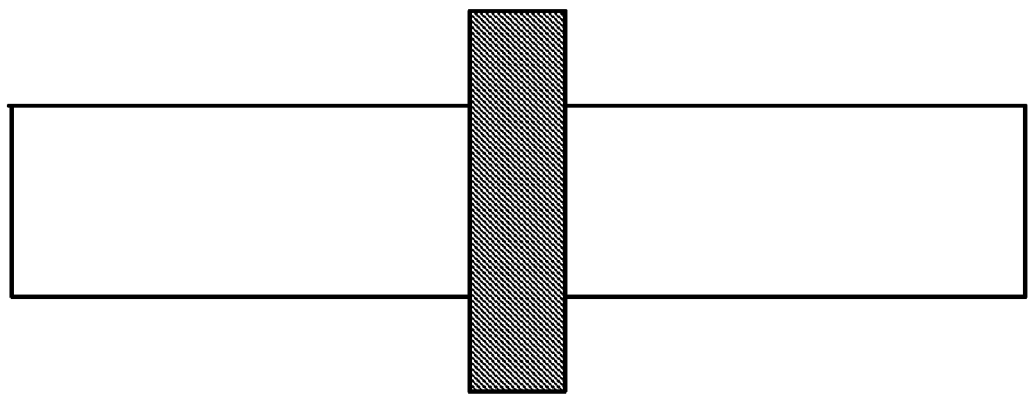
Figure 12:
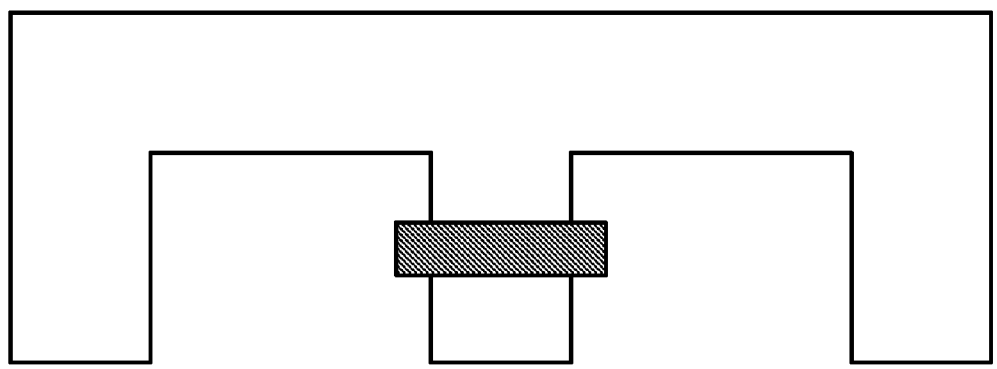

As shown in FIG. 9, the magnetic core may be arc-shaped core having a wire wound around any portion of its axis. Alternatively, as shown in FIGS. 10 and 11, the core may be a linear-shaped structure having perpendicular or chamfered ends with respect to its main axis. In both cases, a wire may be wound around any portion of its axis. The wound wire may be a single strand and or multiple strands in parallel electrically. The wire may include a metal sheet of conductive material with or without insulation, and or an extruded magnet wire with or without insulation. Also, as shown in FIG. 12, the core may have more than 2 poles with windings around one or more of the poles.

It should be appreciated that the construction, size and shape of the core may be made to be dependent upon how the windings will be installed on the core component. For example, certain embodiments contemplate windings that are wound directly around and/or on the core. Also, other embodiments may include windings that are wound on a sleeve or bobbin that is slipped over a portion of the core, or are wound on a mandrel, potted and removed for subsequent assembly onto the core. It should be appreciated that certain embodiments may include a combination of the these approaches. A channel may be cut into the face of the pole in order to allow windings or wire to be installed. For example, a shorted turn may be inserted into the channel and connected together outside of the channel.

The wire used for the windings may be insulated to prevent closely wound, adjacent turns from shorting out. In the context of directly wound windings, the wire may be of such a gauge as to prevent the core from cutting through the insulation, for example with sharp surfaces or edges. Therefore, to accommodate such directly wound cores, the core may have a smooth winding surface, or in some cases may provide a corner radius to accommodate the turns.

The bobbin may be a structure that includes a single bobbin or multiple bobbins. The bobbin may provide insulation properties with respect to the rest of the core, as well as providing operation and safety capabilities. The wire may be wound around the pole faces of the core. Where wire is wound around two or more poles, the number of turns of the winding may be equal between both poles. Also, the wire may be wound around a central point of the core, instead of or in addition to being wound around the pole faces of the core. Where wound around both, the number of turns of the winding around the pole faces may be a fraction of the number of turns around the central point of the core.

Again, it should be appreciated that fabrication of a core by pressing ferromagnetic powder into a mold allows a diverse range of core shapes and therefore more varied winding solutions. For example, in one embodiment of a distributed gap core a bobbin may be more readily used to accurately prefabricate and position the winding on the core.

Figure 1B:
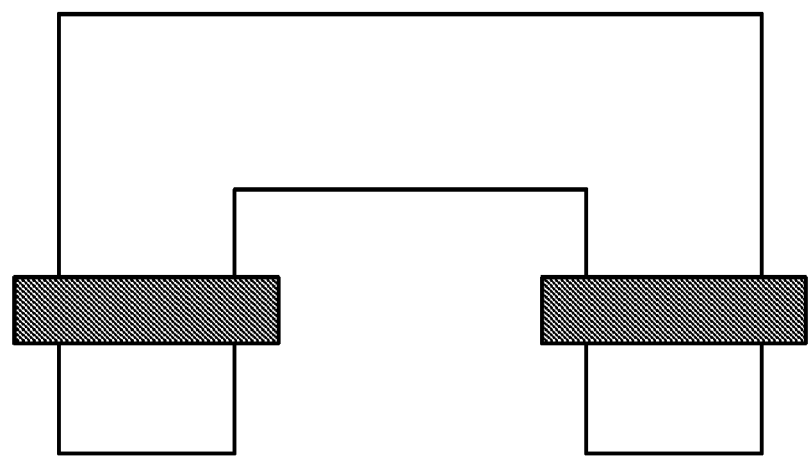
Figure 2A:
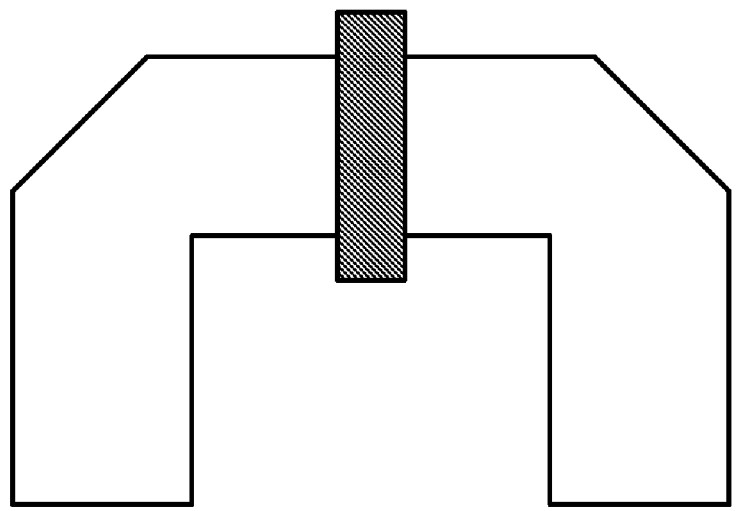
Figure 2B:
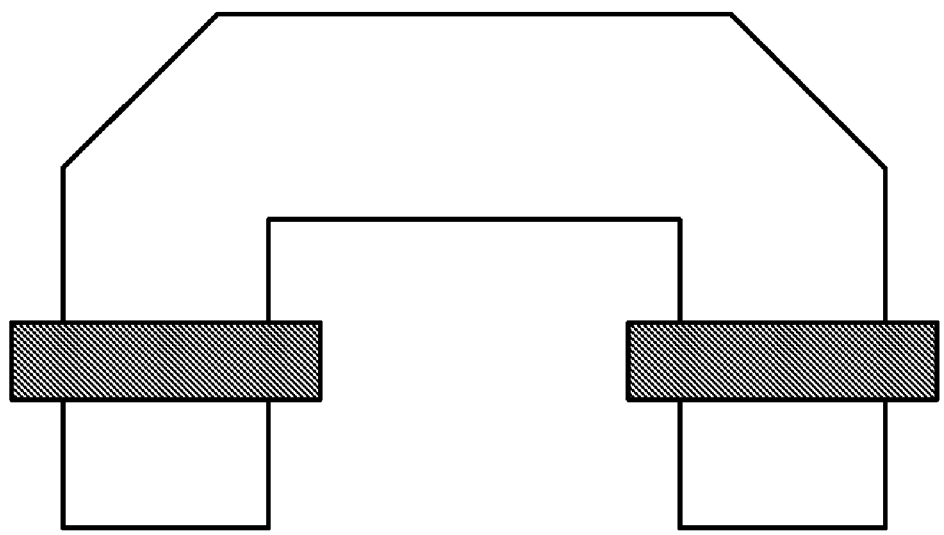
Figure 3A:
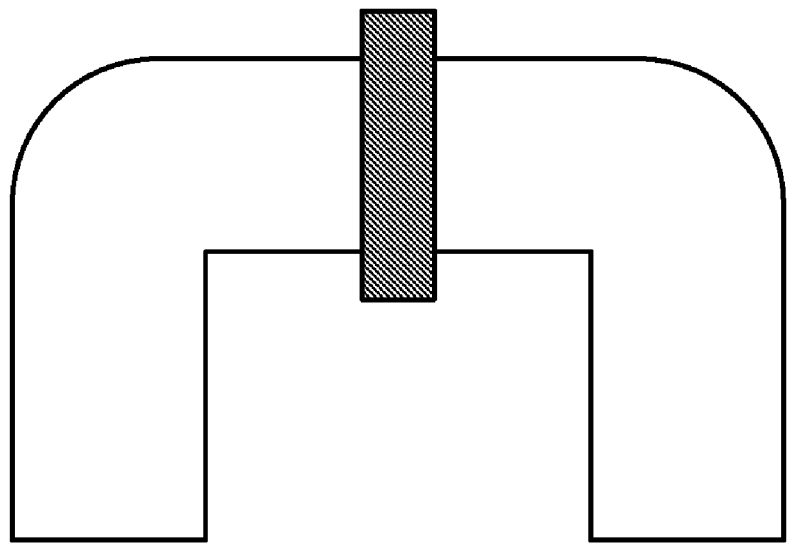
Figure 3B:
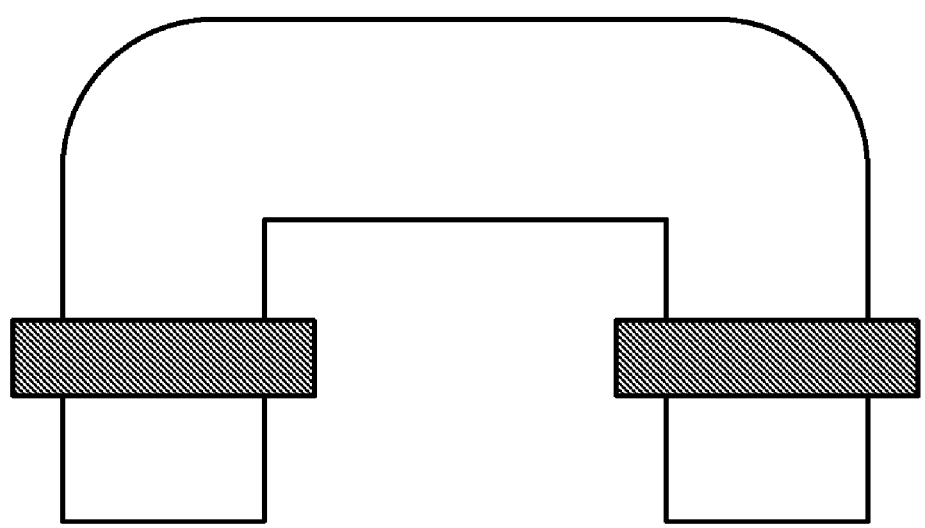

FIGS. 1B, 2B and 3B illustrate how one or more wires may be wound around at least a portion of the magnetic core. As shown in FIGS. 1B, 2B and 3B, the windings may be wound around the first and third sections of the core. Such a winding may be a single winding wound around the first and third sections, or two or more individual windings each wound around the first and third sections. Alternatively, as shown in FIGS. 1A, 2A and 3A, the winding may be wound around the second section of the core. Again, the core winding may be a single winding or multiple windings.

Figure 14:
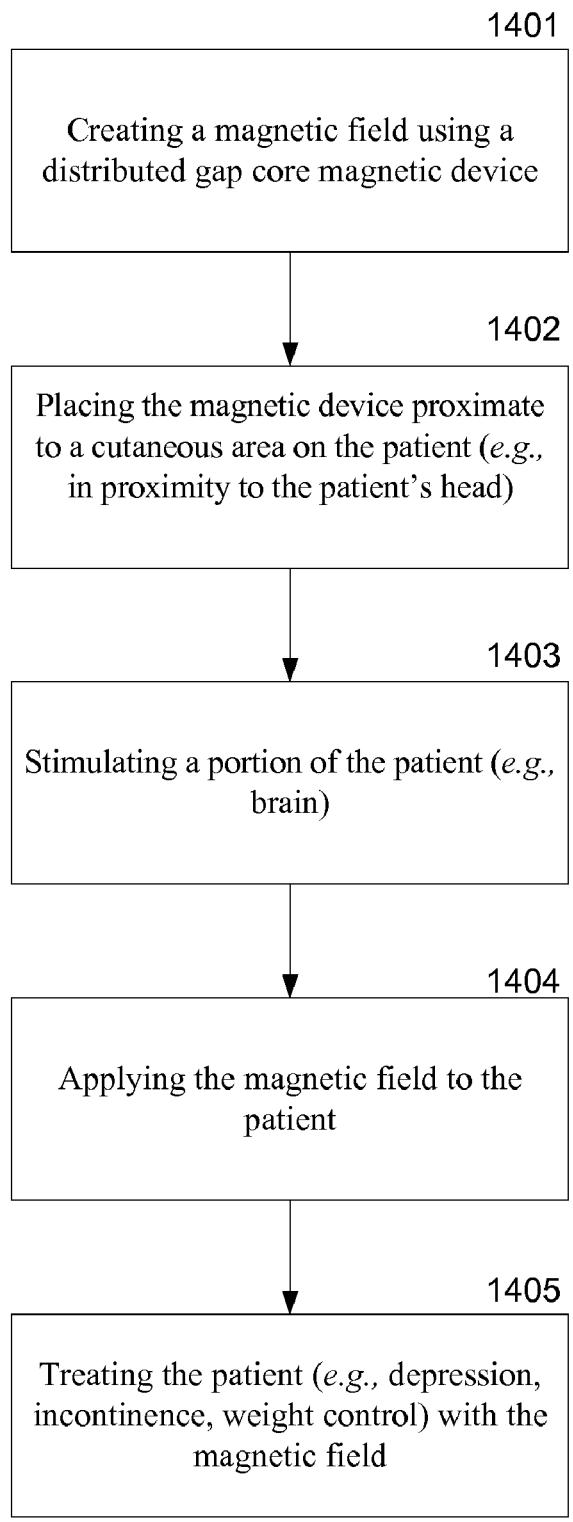
FIG. 14 is a flow diagram of a method for treating a patient.

FIG. 14 is a flow diagram of a method for treating a patient. As shown in FIG. 14, in 1401 a magnetic field is created using a distributed gap core magnetic device. In 1402, the magnetic device is placed proximate to a cutaneous area on the patient, for example, in proximity to the patient's head. In 1403, a portion of the patient's anatomy that is desired to be treated (e.g., brain) is stimulated. In 1404, the magnetic field is applied to the patient. In 1405, the patient is treated, for example for depression, incontinence, and weight control, with the magnetic field. Other types of conditions also may be treated using these techniques. These may include, but are not limited to, treating the peripheral nervous system, rehabilitating the patient's muscle.

It also should be appreciated that the described techniques further may be used to directly diagnose a patient's condition. Also, the techniques may be used to diagnose a response to drugs or other therapy and/or to quantify effectiveness of such therapies. In just one of many possible examples, pharmaceuticals may have effects (i.e., direct or secondary) on the performance of the central nervous system. These effects may be observed by providing stimulation (e.g., TMS) and observing evoked potentials, motor response, conduction velocities or other responses, just to name a few of the many contemplated observed effects. Changes in response may be used to quantify performance or to determine optimal dosing, for example.

In addition, many pathologies may be diagnosed using the described techniques an investigative tool to observe neurological response. Such pathologies include, but are not limited to, degenerative diseases, extent of traumatic injury, progression of diseases, systemic deficiencies, and congenital anomalies (e.g., tinnitus). A partial list of such conditions is provided here for the purposes of further understanding. However, the scope of the described embodiments are not limited to this list. These include assessment or measuring effect of pharmaceuticals, including anti-convulsives, Alzheimer's medications, anti-psychotics, pain medications, anti-anxiety, hypnotics (sedatives), analgesics (central), ADHD medications and, anesthetics. Just a few of the contemplated diagnostic applications include compromised motor function, degenerative diseases (e.g., Alzheimer's, Parkinson's, Amyotrophic Lateral Sclerosis), multiple sclerosis, diabetic neuropathy, chronic demyelinating neuropathy, acute demyelinating neuropathy, epilepsy, vitamin B12 deficiency (e.g., pernicious anemia), vitamin E deficiency, neurosarcoidosis, tinnitus, and stroke rehabilitation.

Other disorders may also be treated with the described techniques including treating a patient such as a human suffering from major depressive disorder, epilepsy, schizophrenia, Parkinson's disease, Tourette's syndrome, amyotrophic lateral sclerosis (ALS), multiple sclerosis (MS), Alzheimer's disease, attention deficit/hyperactivity disorder, obesity, bipolar disorder/mania, anxiety disorders (panic disorder with and without agoraphobia, social phobia also known as social anxiety disorder, acute stress disorder, generalized anxiety disorder), post-traumatic stress disorder (one of the anxiety disorders in DSM), obsessive compulsive disorder (one of the anxiety disorders in DSM), pain (migraine, trigeminal neuralgia) (also: chronic pain disorders, including neuropathic pain, e.g., pain due to diabetic neuropathy, post-herpetic neuralgia, and idiopathic pain disorders, e.g., fibromyalgia, regional myofascial pain syndromes), rehabilitation following stroke (neuro plasticity induction), tinnitus, stimulation of implanted neurons to facilitate integration, substance-related disorders (dependence and abuse and withdrawal diagnoses for alcohol, cocaine, amphetamine, caffeine, nicotine, cannabis), spinal cord injury & regeneration/rehabilitation, head injury, sleep deprivation reversal, primary sleep disorders (primary insomnia, primary hypersomnia, circadian rhythm sleep disorder), cognitive enhancements, dementias, premenstrual dysphoric disorder (PMS), drug delivery systems (changing the cell membrane permeability to a drug), induction of protein synthesis (induction of transcription and translation), stuttering, aphasia, dysphagia, essential tremor, or eating disorders (bulimia, anorexia, binge eating).

The method further may include determining so-called "motor threshold" of the patient. More specifically, the magnetic device may be moved over a particular area until some indication of positioning is provided. For example, in the context of magnetic stimulation of the brain, the magnetic device may be moved over the patient's head until the patient's thumb moves or twitches indicating a motor threshold point. This motor threshold determination may be at a similar or different frequency, for example, using a stimulation frequency rate of 1 Hz.

From this point, the magnetic device may be moved to a desired treatment location. For example, for TMS treatment of the brain, the magnetic device may located approximately 5 centimeters anteriorly from motor threshold point. During TMS treatment, in some embodiments, the stimulator output may be set to approximately 110% of relaxed motor threshold with perhaps a repetition rate of approximately 10 Hz.

Figure 15:
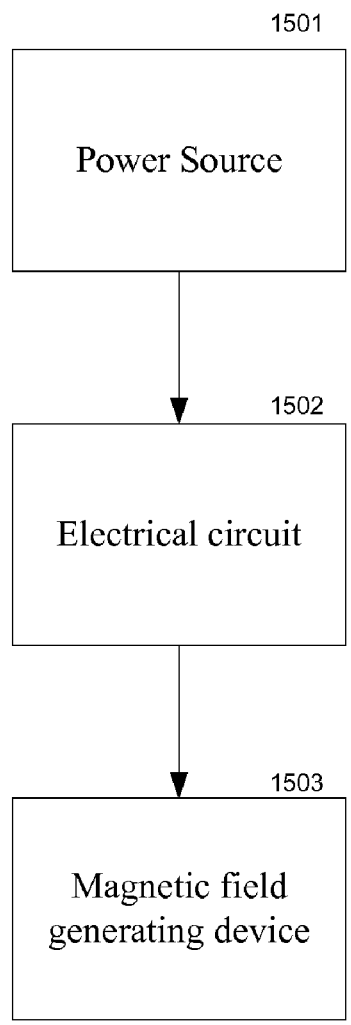
FIG. 15 is a block diagram of a system for treating a patient.

FIG. 15 is a block diagram of a system for treating a patient. As shown in FIG. 15, a system 1500 for treating a patient includes a magnetic field generating device 1501. Magnetic field generating device 1501 may have a distributed gap core structure. Also, a circuit 1502 is in electrical communication with the magnetic field generating device.

The circuit may be act as a switch to pulse the magnetic field generating device in such a way to treat the desired condition. In this way, the magnetic field may be applied to the patient in cycles intermittently. The exact stimulation frequency or frequency in which the magnet is pulsed may be varied depending upon the particular application (e.g., size of magnet and area of stimulation). For example, in just some embodiments, it may be desirable to stimulate for a five second period, followed by rest for a five second period and then repeat stimulation continuously for another five seconds. While they are being stimulated, it is desirable to have the muscle groups continuously excited. This requirement dictates the necessity of continuing to pulse the cores at a repetition rate of 15 Hz. Because of the large currents involved during any given firing of the core, it is necessary to make the cores as efficient as possible. It is desirable to focus the magnetic field into the region targeted for stimulus to the exclusion of surrounding regions. The specially designed cores offered by this invention realize that focusability.

In addition, a power source 1503 may be in electrical communication with the circuit. The power source may provide direct current (dc) or alternating current (ac) power. Also, the power levels may be consistent with those available in residential and commercial settings.

Figure 16:
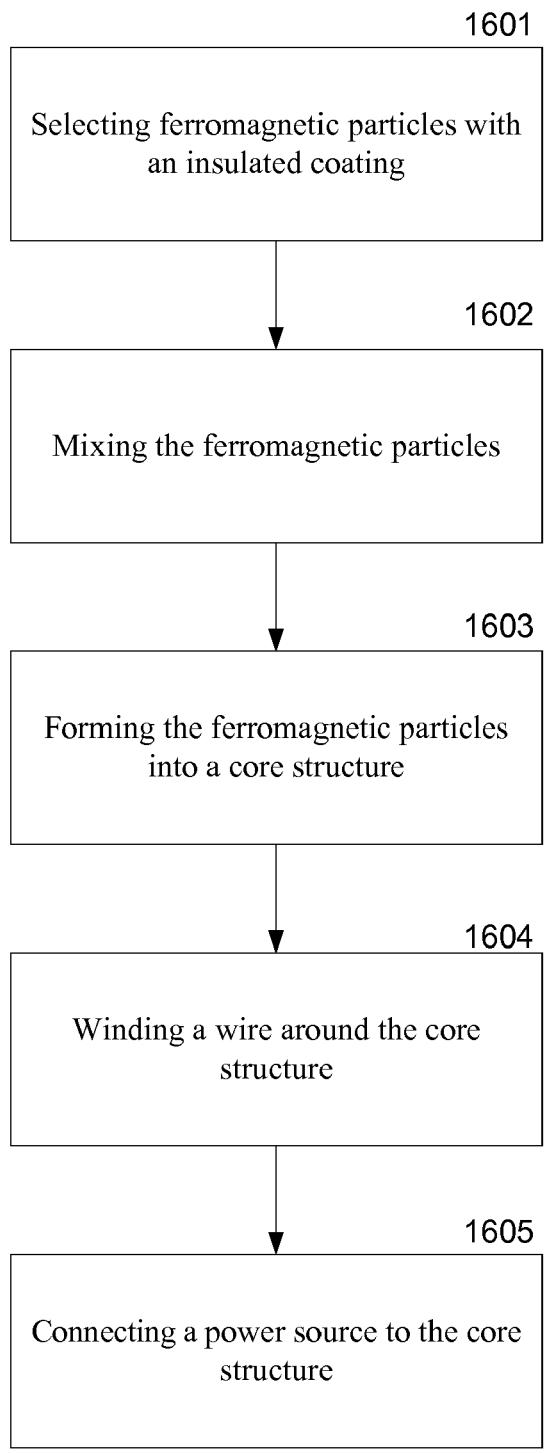
FIG. 16 is a flow diagram of a method for manufacturing a magnetic core for treating a patient.

FIG. 16 is a flow diagram of a method for manufacturing a magnetic core for treating a patient. As shown in FIG. 16, in 1601, ferromagnetic particles are selected with an insulated coating. In 1601, the ferromagnetic particles are mixed and in 1602, the ferromagnetic particles are formed into a core structure. In 1604, a conductor (e.g., wire) is wound around the core structure. In 1605, a power source is connected to the core structure.

Although not shown for the purposes of brevity, it should be appreciated that similar winding configurations may be applied to any of the possible core shapes, illustrated in the figures or otherwise. The description herein with regard to the shapes and winding configurations of the core have been provided to facilitate the discussion and understanding of the many possible shapes and configuration that are within the scope of the contemplated embodiments. Similarly, it should be appreciated that these shapes and configurations are equally applicable to any type of magnetic core used for treating and/or diagnosing a patient, including but not limited to pressed powder, sintered, tape wound, and coil only or "air" core structures.

It is to be understood that the foregoing illustrative embodiments have been provided merely for the purpose of explanation and are in no way to be construed as limiting of the invention. Words used herein are words of description and illustration, rather than words of limitation. In addition, the advantages and objectives described herein may not be realized by each and every embodiment practicing the present invention. Further, although the invention has been described herein with reference to particular structure, materials and/or embodiments, the invention is not intended to be limited to the particulars disclosed herein. Rather, the invention extends to all functionally equivalent structures, methods and uses, such as are within the scope of the appended claims.

For example, although a great deal of the discussion was based on the use of a pressed powder distributed gap core structure, it should be appreciated that the contemplated embodiments include the use of any core structure, including "air core," non-sintered, and other ferromagnetic core structures for example. Moreover, although certain core shapes and configurations have been described herein, it should be appreciated that the shapes are provided merely to provide an understanding of the many core shapes contemplated by the embodiments.

In addition, although the disclosure addresses the treatment of patients, it should be appreciated that techniques described herein also contemplate patient diagnosis. In fact, where the disclosure refers to the treatment of patients for certain conditions, the techniques equally apply to the monitoring and diagnosis of patients for the same or similar conditions.

Those skilled in the art, having the benefit of the teachings of this specification, may affect numerous modifications thereto and changes may be made without departing from the scope and spirit of the invention.

What is claimed:

1. A method of treating a patient, comprising:
    creating a magnetic field using a magnetic device having a distributed gap core structure that is adapted for use in connection with transcutaneous magnetic stimulation, wherein the distributed gap core structure comprises a matrix of non-conductive gaps;
    applying the magnetic field to the patient; and
    treating the patient as a function of the magnetic field.

2. The method of claim 1, further comprising creating the distributed gap core structure by at least one of the following: machining, pressing, molding, gluing, and extruding.

3. The method of claim 1, further comprising creating the distributed gap core structure by at least one of the following processes: gluing and attaching individual core structures.

4. The method of claim 1, further comprising determining motor threshold.

5. The method of claim 4, further comprising determining a stimulation point as a function of the determined motor threshold.

6. The method of claim 1, further comprising positioning the patient with respect to the magnetic device.

7. The method of claim 1, further comprising positioning the magnetic device with respect to the patient.

8. The method of claim 1, further comprising providing a pulse train of stimulation signals.

9. The method of claim 1, wherein the distributed gap core structure comprises a powder of ferromagnetic particles coated with an insulative substance.

10. The method of claim 9, wherein the ferromagnetic particles comprises at least one of the following: a ferromagnetic electrically conductive material, iron, copper, brass and aluminum.

11. The method of claim 1, further comprising securing the patient with respect to the magnetic device.

12. The method of claim 1, further comprising treating the patient via diagnosis.

13. The method of claim 1, further comprising placing the magnetic device in proximity to the patient's head and treating depression.

14. The method of claim 1, further comprising stimulating a portion of the patient's brain and treating depression.

15. The method of claim 1, wherein the magnetic device provides the transcutaneous magnetic stimulation.

16. The method of claim 15, wherein the magnetic device comprises a magnetic core that saturates at 0.5 Tesla or greater.

17. The method of claim 15, wherein the magnetic device comprises a magnetic core with a non-toroidal geometry.

18. The method of claim 1, further comprising placing the magnetic device proximate to a cutaneous surface.

19. The method of claim 18, further comprising stimulating at least one of the following relatively proximate to the cutaneous surface: tissue, nerves and muscle.

20. The method of claim 19, wherein the tissue is brain tissue.

21. The method of claim 1, further comprising locating a conductor on a treatment area relative to a first location.

22. The method of claim 21, further comprising reducing stimulation of a cutaneous-proximate area on the patient.

23. The method of claim 22, wherein the reducing comprises modifying an electric field created by the transcutaneous magnetic stimulation.

24. The method of claim 23, wherein the modification of the electric field occurs through modification of a magnetic flux created by the transcutaneous magnetic stimulation.

25. The method of claim 24, wherein the reducing comprises modifying the magnetic field created by the transcutaneous magnetic stimulation.

26. The method of claim 1, wherein the core has a non-linear shape.

27. The method of claim 1, further comprising treating the patients' peripheral nervous system.

28. The method of claim 1, further comprising treating incontinence.

29. The method of claim 1, further comprising treating the patient for weight control.

30. The method of claim 1, further comprising rehabilitating the patient's muscle.

31. The method of claim 1, further comprising applying the magnetic field in cycles intermittently.

32. The method of claim 1, further comprising maintaining a temperature of the magnetic device at or below 41.5 degrees Celsius.

* * * * *